(12) United States Patent
Kim et al.

(10) Patent No.: US 11,472,840 B2
(45) Date of Patent: Oct. 18, 2022

(54) ACETYLCHOLINE RECEPTOR-BINDING PEPTIDE

(71) Applicant: AMICOGEN, INC., Jinju-si (KR)

(72) Inventors: Sung Hyun Kim, Sejong (KR); Won Il Choi, Seoul (KR); Yong Chul Shin, Jinju-si (KR); Jeung Hoon Lee, Daejeon (KR); Young Sung Yun, Jinju-si (KR); Jin Hwa Kim, Daejeon (KR)

(73) Assignee: SKINMED CO., LTD., Daejeon (KR)

( * ) Notice: Subject to any disclaimer, the term of this patent is extended or adjusted under 35 U.S.C. 154(b) by 0 days.

(21) Appl. No.: 16/626,774

(22) PCT Filed: Jun. 25, 2018

(86) PCT No.: PCT/KR2018/007170
§ 371 (c)(1),
(2) Date: Dec. 26, 2019

(87) PCT Pub. No.: WO2019/004674
PCT Pub. Date: Jan. 3, 2019

(65) Prior Publication Data
US 2020/0123199 A1  Apr. 23, 2020

(30) Foreign Application Priority Data
Jun. 28, 2017 (KR) .................. 10-2017-0082039

(51) Int. Cl.
| | |
|---|---|
| *C07K 7/06* | (2006.01) |
| *A61K 8/64* | (2006.01) |
| *A61Q 19/08* | (2006.01) |
| *G01N 33/68* | (2006.01) |

(52) U.S. Cl.
CPC ............... *C07K 7/06* (2013.01); *A61K 8/64* (2013.01); *A61Q 19/08* (2013.01); *G01N 33/6845* (2013.01); *G01N 2333/705* (2013.01)

(58) Field of Classification Search
None
See application file for complete search history.

(56) References Cited

U.S. PATENT DOCUMENTS

| | | |
|---|---|---|
| 2012/0122803 A1 | 5/2012 | McIntosh |
| 2012/0220539 A1 | 8/2012 | McIntosh |
| 2015/0361137 A1 | 12/2015 | Zhmak et al. |

FOREIGN PATENT DOCUMENTS

| | | |
|---|---|---|
| JP | 2997850 B2 | 1/2000 |
| JP | 2012-505929 A | 3/2012 |
| KR | 10-2011-0117038 A | 10/2011 |
| KR | 1020110117038 A | 10/2011 |
| WO | WO 2013/062444 A1 | 5/2013 |

OTHER PUBLICATIONS

BLAST search results for RKSLLR (retrieved from https://blast.ncbi.nlm.nih.gov/Blast.cgi on May 5, 2021, 15 pages) (Year: 2021).*
Kuan et al. ('A novel neuroprotective therapy for Parkinson's disease using a viral noncoding RNA that protects mitochondrial complex I activity' The Journal of Experimental Medicine v209(1) 2012 pp. 1-10) (Year: 2012).*
Park et al. ('A high-affinity peptide for nicotinic acetylcholine receptor-alpha1 and its potential use in pulmonary drug delivery' Journal of Controlled Release v192 2014 pp. 141-147) (Year: 2014).*
Wan Jingjing, et al., "alpha Conotoxin Dendrimers Have Enhanced Potency and Selectivity for Homomeric Nicotinic Acetylcholine Receptors", Journal of the American Chemical Society, vol. 137, No. 9, Mar. 3, 2015, pp. 3209-3212.
Seho Park, et al., "A high-affinity peptide for nicotinic acetylcholine receptor-a1 and its potential use in pulmonary drug delivery", Journal of Controlled Release, vol. 192, pp. 141-147, 2014.
WIPO, International Search Report dated Nov. 13, 2018.

* cited by examiner

*Primary Examiner* — Ronald T Niebauer
(74) *Attorney, Agent, or Firm* — Li & Cai Intellectual Property (USA) Office

(57) ABSTRACT

The present disclosure relates to an acetylcholine receptor-binding peptide and, more particularly, to novel peptides which exhibit a wrinkle amelioration effect by binding the peptides to an acetylcholine receptor on which acetylcholine acts, thereby blocking secretion of acetylcholine. Peptides according to the present disclosure suppress secretion of acetylcholine by having a high binding strength with the acetylcholine receptor, thereby strongly binding the peptides to acetylcholine. Therefore, a cosmetic composition and a pharmaceutical composition comprising the peptides according to the present disclosure as an active ingredient exhibit an excellent wrinkle ameliorating effect.

3 Claims, 7 Drawing Sheets

Specification includes a Sequence Listing.

[Fig. 1]
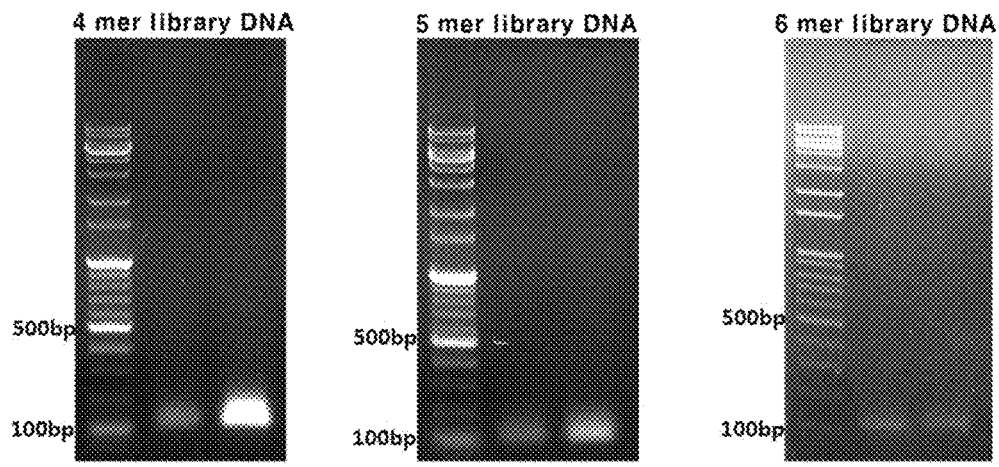
[Fig. 2]
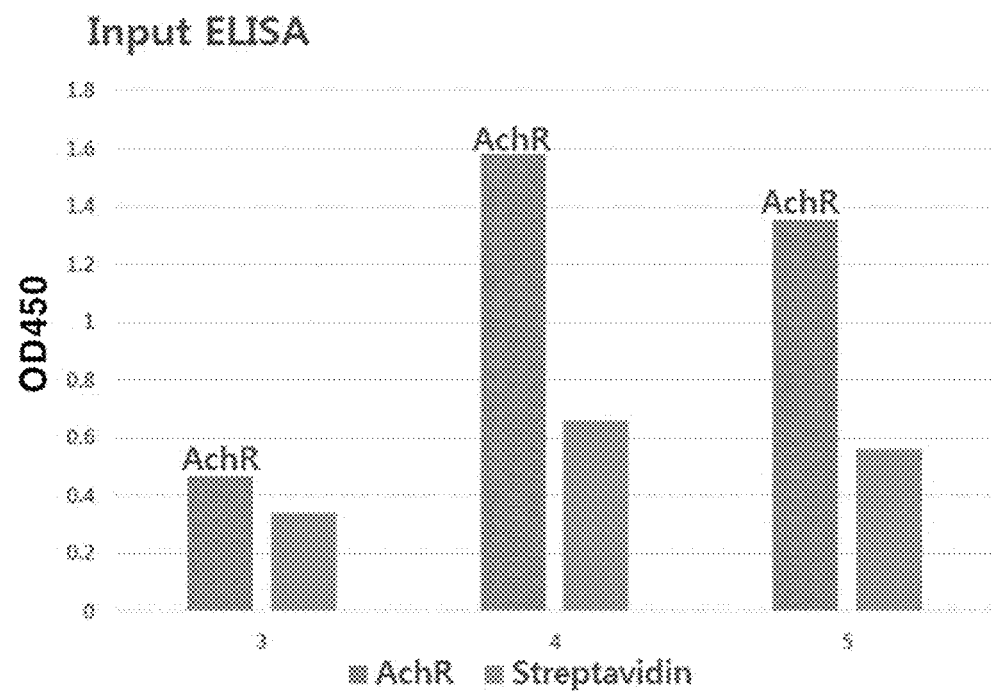

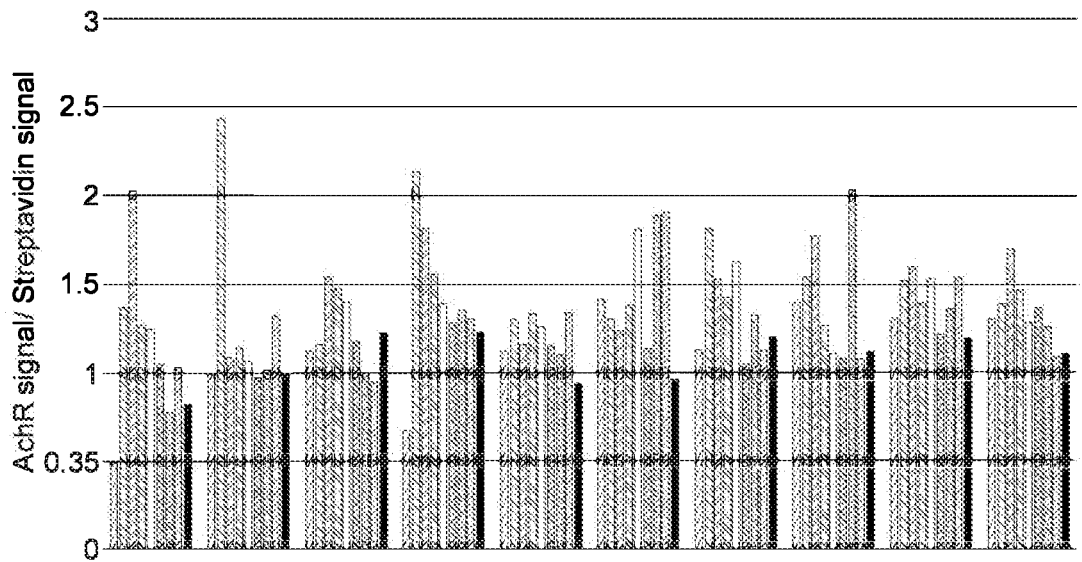
[Fig. 3]
[Fig. 4]
| S6_11 | WIWKGEIYDSK | SEQ ID NO : 22 |
| S6_10 | WIWKGNKQVKF | SEQ ID NO : 21 |
| S6_9 | WIWKGLYQRLG | SEQ ID NO : 20 |
| S6_7 | WIWKGRQLNNQ | SEQ ID NO : 19 |
| S6_8 | WIWKGDNLQNN | SEQ ID NO : 18 |
| S6_6 | WIWKGGRLSAS | SEQ ID NO : 17 |
| S6_5 | WIWKGQLGQLS | SEQ ID NO : 16 |
| S6_1 | WIWKGKGTLNR | SEQ ID NO : 23 |
| S6_2 | WIWKGRKSLLR | SEQ ID NO : 24 |
| S6_3 | WIWKGEDKGKN | SEQ ID NO : 25 |
| S6_4 | WIWKGRDKLQM | SEQ ID NO : 26 |

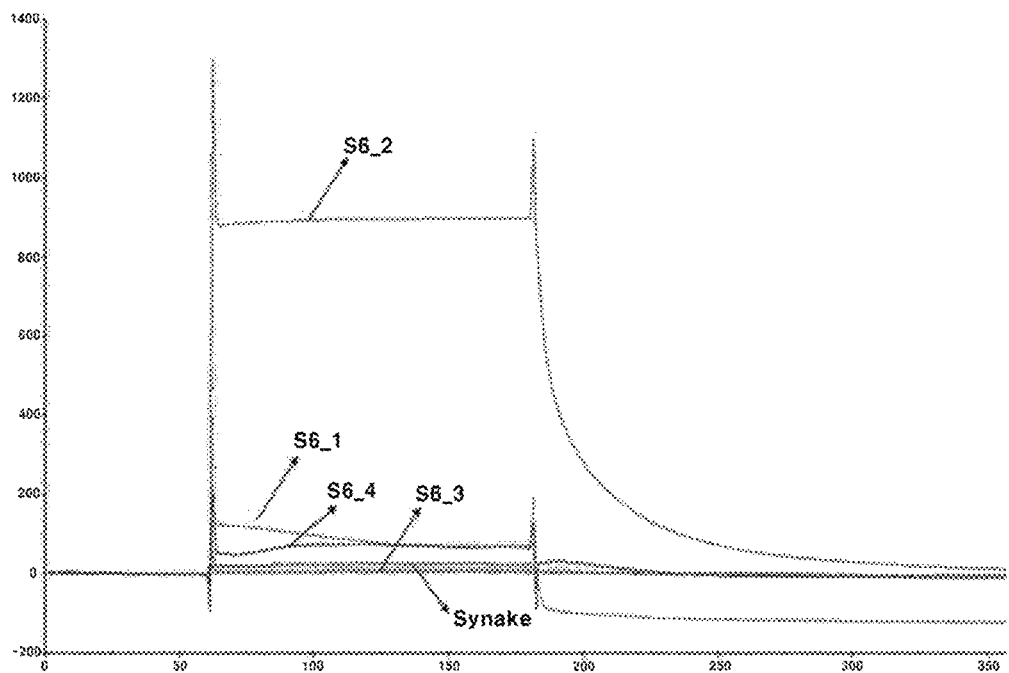
[Fig. 5]

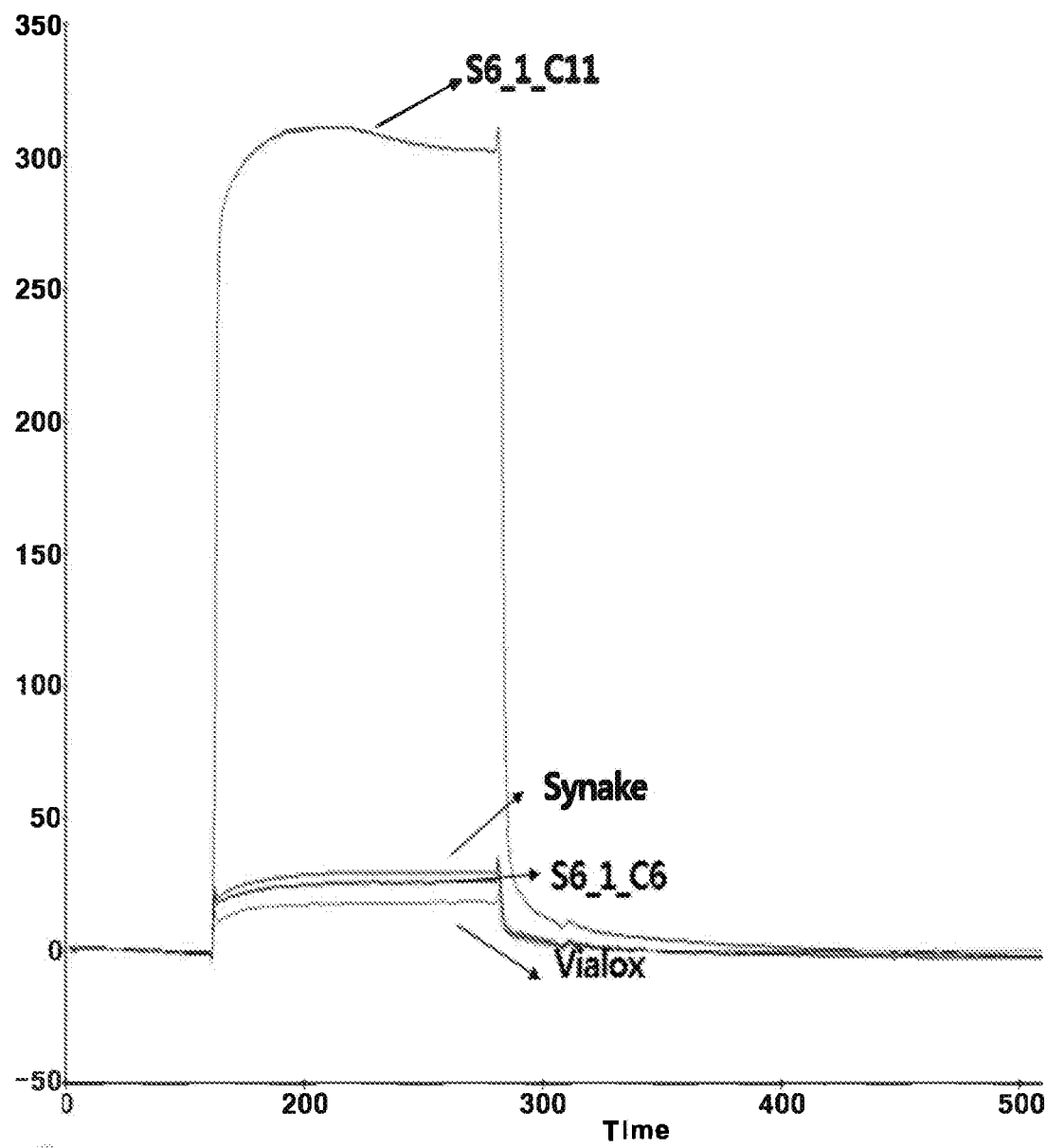
[Fig. 6]

[Fig. 7]
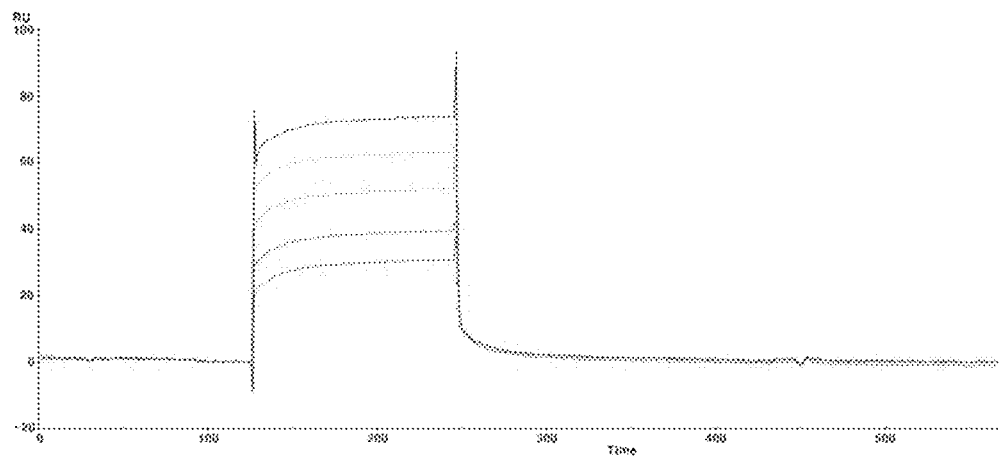
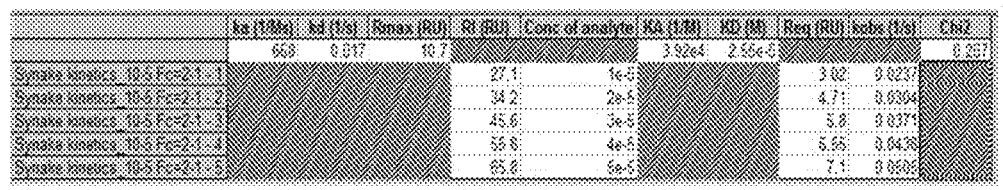
[Fig. 8]
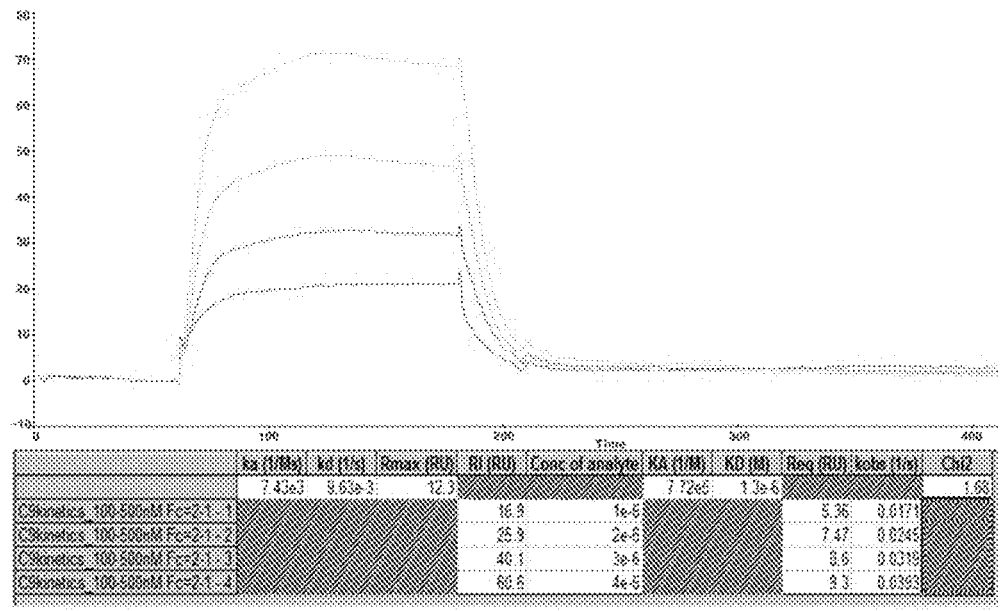

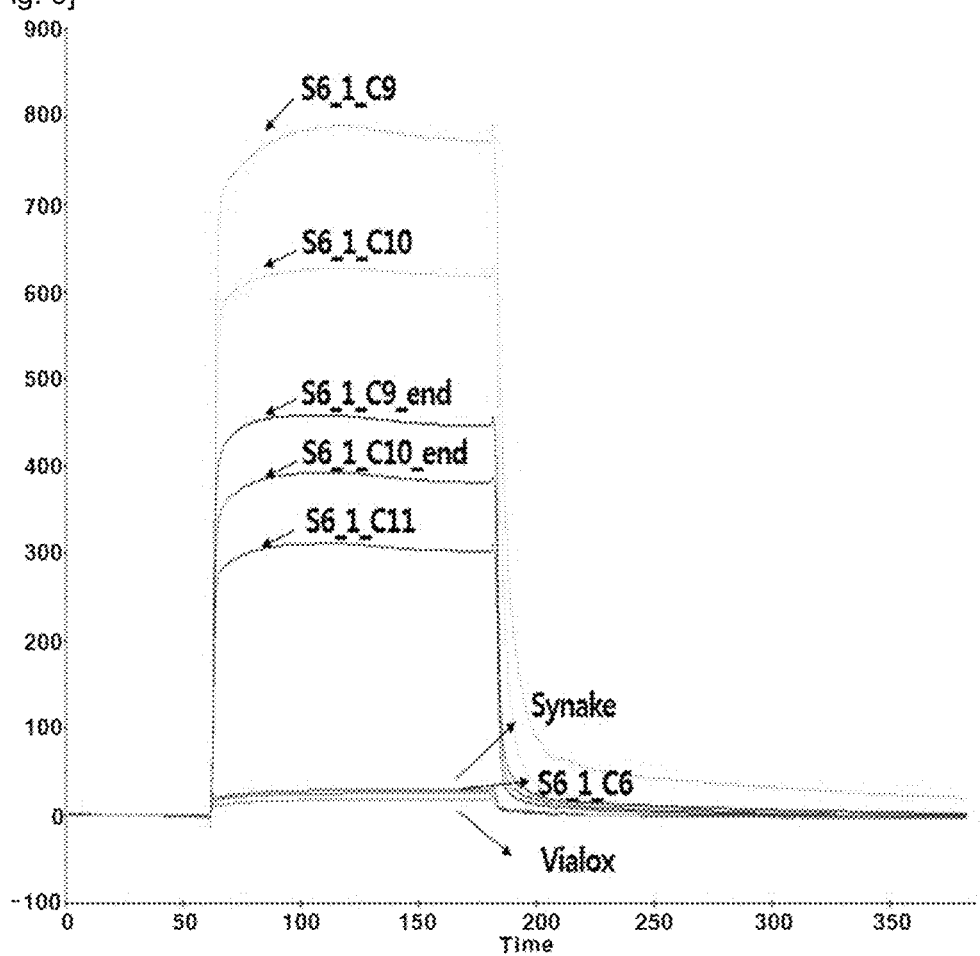

[Fig. 10]
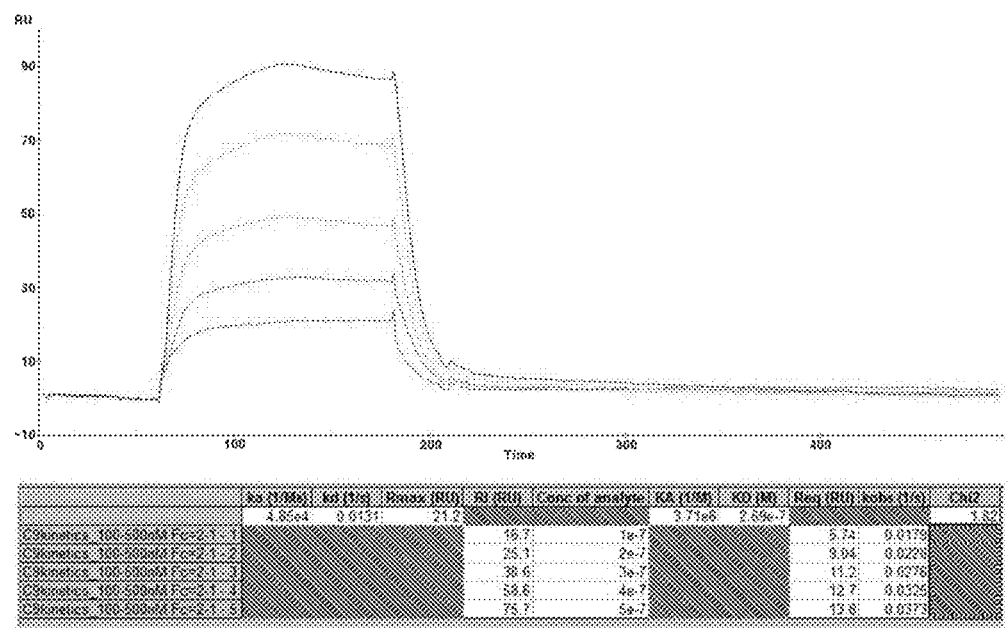

ACETYLCHOLINE RECEPTOR-BINDING PEPTIDE

BACKGROUND OF THE INVENTION

Field of the Invention

The present disclosure relates to an acetylcholine receptor-binding peptide and, more particularly, to peptides which exhibit a wrinkle amelioration effect by binding the peptides to an acetylcholine receptor on which acetylcholine acts, thereby blocking secretion of acetylcholine.

Related Art

Recently, consumers' needs for cosmetics have been gradually changed from requesting uses for decorating themselves beautifully to requesting functional uses of the cosmetics due to an increase in interest for healthy life, improvement of the standard of living, an increase in the entry of women in public affairs, the acceleration of aging, etc.

Research activities intended for developing bioactive substances having a wrinkle amelioration effect has consistently progressed to prevent skin aging phenomenon and maintain more healthy and elastic skin. Typically, tretinoin (trans-retinoic acid) as a therapeutic agent for improving photoaged skin received United States FDA permission in 1995, and wrinkle ameliorating cosmetics have been started to be marketed in earnest while retinol having less side effects than tretinoin has been used in raw materials for cosmetic products from the middle and late 1990s. Thereafter, female hormone-like substances, antioxidants extracted from various plants, etc. as wrinkle ameliorating raw materials have been introduced into cosmetics.

However, most of such raw materials for cosmetic products have been had various problems including inept efficacy, causing of skin side effects, etc. Further, the present raw materials for cosmetic products have not been able to sufficiently satisfy needs of consumers wanting newer, stronger and more fundamental amelioration of wrinkles since the present raw materials for cosmetic products have limited application ranges to the skin, and most of the present raw materials for cosmetic products are similar in efficacies on the skin such as promotion of collagen synthesis, inhibition of collagen decomposition, and removal of active oxygen although present raw materials for cosmetic products are raw materials with good efficacies. Accordingly, researches on raw materials and technologies which are capable of establishing new skin aging mechanisms, and blocking or delaying skin aging based on recent dermatological theories have been actively progressed in cosmetic industries.

Recently, a study of ameliorating skin wrinkles by using a peptide component in cosmetics has been actively proceeded. Peptides, as material formed by coupling two or more amino acids, are produced by chemical synthesis, enzyme reaction, or hydrolysis from protein.

On the other hand, acetylcholine is involved in movements of skeletal muscles and visceral muscle in the peripheral nervous system, and has an effect on learning and memory in the brain. When secretion of acetylcholine, i.e., neurotransmitter is hindered at places where a motor nerve and muscles meet, acetylcholine inhibits contraction of the muscles such that wrinkles are spread while the muscles are being paralyzed. Botox corresponds to an example using this. Botox blocks a process of secreting acetylcholine, i.e., material that is essential in contraction of the muscles at a motor nerve terminal. As a result, the muscles cannot be moved, and wrinkles caused by the muscles are removed.

Therefore, if peptides of inhibiting secretion of acetylcholine are developed by the same principle, it is predicted that amelioration and prevention of skin wrinkles can be expected.

PRIOR ART DOCUMENT

Patent Document (Patent document 1) Korea Patent Registration Publication No. 10-0553174

SUMMARY OF THE INVENTION

The purpose of the present disclosure is to provide peptides which suppress secretion of acetylcholine by binding the peptides to an acetylcholine receptor.

To achieve the purpose, an acetylcholine receptor-binding peptide comprising an amino acid sequence represented by any one of the following general formula 1 according to an aspect of the present disclosure is provided:

| | |
|---|---|
| WTWKG(SEQ ID NO:32)-$X_n$ | [General Formula 1] |
| TWKG(SEQ ID NO:33)-$X_n$ | [General Formula 2] |
| WKG-$X_n$ | [General Formula 3] |
| KG-$X_n$ | [General Formula 4] |
| G-$X_n$ | [General Formula 5] |
| $X_n$ | [General Formula 6] | wherein the $X_n$ indicates a sequence comprised of 1 to 6 any amino acids.

The term in the present disclosure, "peptides or fragments thereof", means a polymer comprised of two or more amino acids connected by an amide bond (or peptide bond). For the purpose of the present disclosure, the peptides or the fragments thereof means peptides which exhibit a wrinkle amelioration effect or fragments thereof.

Peptides or fragments thereof of the present disclosure may include an additional amino acid sequence devised as a specific purpose for increasing stability of targeting sequence, tag, labelled residues, half-life or peptides.

Peptides or fragments thereof of the present disclosure may be obtained by various methods well known in the art. Specifically, peptides or fragments thereof of the present disclosure may be produced by using genetic recombination or protein expression system, or may be produced by a method of synthesizing the peptides or the fragment thereof in vitro through chemical synthesis such as peptide synthesis, and a cell-free protein synthesis method.

More specifically, although the peptides or the fragment thereof not only may be synthesized by a method well known in the art, e.g., an automatic peptide synthesizer, but also may be produced by genetic engineering technology, the present disclosure is not limited thereto. For example, desired peptides can be produced by cutting and separating peptides according to the present disclosure from the fusion protein by using protease or a compound after preparing a fusion gene which encodes a fusion protein formed of a fusion partner and peptides according to the present disclosure through gene manipulation, transforming the fusion gene into a host microbe, and expressing the host microbe in the form of a fusion protein. To this end, for instance, a DNA sequence encoding amino acid residues which can be cut by protease such as Factor Xa or enterokinase and a compound such as CNBr or hydroxylamine may be inserted between the fusion partner and a peptide gene of the present disclosure.

In peptides which suppress secretion of acetylcholine by binding the peptides to an acetylcholine receptor of the present disclosure, the $X_n$ may have any one amino acid sequence among the following SEQ ID NO: 1 to SEQ ID NO: 11:

KGTLNR, [Sequence number 1]

RKSLLR, [Sequence number 2]

EDKGKN, [Sequence number 3]

RDKLQM, [Sequence number 4]

QLGQLS, [Sequence number 5]

GRLSAS, [Sequence number 6]

RQLNNQ, [Sequence number 7]

DNLQNN, [Sequence number 8]

LYQRLG, [Sequence number 9]

NKQVKF, and [Sequence number 10]

ETYDSK [Sequence number 11]

In peptides which suppress secretion of acetylcholine by binding the peptides to an acetylcholine receptor of the present disclosure, the peptides may comprise any one amino acid sequence among the following SEQ ID NO: 12 to SEQ ID NO: 22:

Sequence number 12: WTWKGKGTLNR,

Sequence number 13: WTWKGRKSLLR,

Sequence number 14: WTWKGEDKGKN,

Sequence number 15: WTWKGRDKLQM,

Sequence number 16: WTWKGQLGQLS,

Sequence number 17: WTWKGGRLSAS,

Sequence number 18: WTWKGRQLNNQ,

Sequence number 19: WTWKGDNLQNN,

Sequence number 20: WTWKGLYQRLG,

Sequence number 21: WTWKGNKQVKF, and

Sequence number 22: WTWKGETYDSK

In peptides which suppress secretion of acetylcholine by binding the peptides to an acetylcholine receptor of the present disclosure, the acetylcholine receptor-binding peptide comprises any one sequence among amino acid sequences represented by the following SEQ ID NO: 23 to SEQ ID NO: 26:

Sequence number 23: WTWKGKGTLNR,

Sequence number 24: WTWKGRKSLLR,

Sequence number 25: WTWKGEDKGKN, and

Sequence number 26: WTWKGRDKLQM

In peptides which suppress secretion of acetylcholine by binding the peptides to an acetylcholine receptor of the present disclosure, the acetylcholine receptor-binding peptide comprises any one sequence among amino acid sequences represented by the following SEQ ID NO: 27 to SEQ ID NO: 31. The amino acid sequences represented by the following SEQ ID NO: 27 to SEQ ID NO: 31 are structures in which some of amino acid sequences represented by the SEQ ID NO: 23 to SEQ ID NO: 26 bear fruit for optimization:

Sequence number 27: TWKGKGTLNR,

Sequence number 28: WKGKGTLNR,

Sequence number 29: WTWKGKGTLN,

Sequence number 30: WTWKGKGTL, and

Sequence number 31: KGTLNR

A method of screening an acetylcholine receptor-binding peptide according to another aspect of the present disclosure is provided. The method comprises the steps of:

(1) preparing a recombinant phage by inserting the peptide library into a vector after preparing a peptide library;

(2) mixing the recombinant phage with an acetylcholine receptor, and biopanning a mixture of the recombinant phage and the acetylcholine receptor to select a phage which is bound to the acetylcholine receptor;

(3) performing an enzyme-linked immunosorbent assay (ELISA) of the acetylcholine receptor and a control group with respect to the phage selected in the step (2); and (4) analyzing performance results of the ELISA to select a phage having an acetylcholine receptor-binding signal intensity of 1.5 time or more compared to the control group.

In a method of selecting peptides which suppress secretion of acetylcholine by binding the peptides to an acetylcholine receptor of the present disclosure, the peptide library in the step (1) of preparing a recombinant phage by inserting the peptide library into a vector after preparing a peptide library may be prepared by using a DNA library comprised of any one base sequence among SEQ ID NO: 1 to SEQ ID NO: 11.

Furthermore, the present disclosure provides a polynucleotide encoding peptides according to the present disclosure. Further, as long as a polynucleotide comprising base sequences showing homology with the base sequence can encode peptides which are capable of showing a bonding activity with respect to the biostructure, the polynucleotide can be also included in a category of the polynucleotide provided in the present disclosure, wherein the polynucleotide may become a polynucleotide comprising base sequences showing preferably 80% or more of homology, more preferably 90% or more of homology, or most preferably 95% or more of homology.

Furthermore, a cosmetic composition for wrinkle amelioration comprising peptides according to the present disclosure as an active ingredient according to another aspect of the present disclosure is provided.

Furthermore, a pharmaceutical composition for wrinkle amelioration comprising the above-mentioned peptides as an active ingredient according to another aspect of the present disclosure is provided.

A pharmaceutical composition for wrinkle amelioration of the present disclosure may comprise peptides according to the present disclosure or pharmaceutically acceptable salts thereof alone, or may further comprise one or more pharmaceutically acceptable carriers, excipients or diluents thereof.

In the present disclosure, the term "pharmaceutically acceptable" means that the salts, carriers, excipients or diluents of the peptides are contained in the pharmaceutical composition in such sufficient amount extents that can exhibit a treatment effect, do not cause side effects, and may be easily determined by a person of ordinary skill in the art according to elements well-known to the medical field including types of diseases, age, weight, health and gender of a patient, sensitivity of the patient to drug, administration route, administration method, administration frequency, treatment period, mixing, a drug simultaneously used, etc.

For example, the pharmaceutically acceptable carriers may further comprise carriers for oral administration or carriers for non-oral administration.

The carriers for oral administration may include lactose, starch, cellulose derivatives, magnesium, stearate, stearic acid, etc. Further, the carriers for non-oral administration may include water, suitable oil, a saline solution, water-based glucose, glycol, etc., and may additionally include a stabilizer and a preservative. A suitable stabilizer may include an antioxidant such as sodium bisulfate, sodium sulfite or ascorbic acid. A suitable preservative may include benzalkonium chloride, methyl- or propyl-paraben, or chlorobutanol. Carriers described in the following document may be referred to as other pharmaceutically acceptable carriers (Remington's Pharmaceutical Sciences, 19th ed., Mack Publishing Company, Easton, Pa., 1995).

A pharmaceutical composition for wrinkle amelioration of the present disclosure can be administered to mammals including human by any method. For example, a pharmaceutical composition for wrinkle amelioration of the present disclosure can be administered by oral administration or non-oral administration. Although the present disclosure is not limited thereto, the non-oral administration may be intravenous administration, intramuscular medication, intraarterial administration, intramedullary administration, intrathecal administration, intraperitoneal administration, dermal administration, subcutaneous administration, intraperitoneal administration, intranasal administration, intestinal administration, topical administration, sublingual administration, or intrarectal administration. Preferably, a pharmaceutical composition according to the present disclosure can be dermally administered. The 'dermal administration' in the above description indicates that an active ingredient contained in the composition according to the present disclosure is enabled to be transferred into the skin by administering a pharmaceutical composition according to the present disclosure into cells or skin. For example, a pharmaceutical composition according to the present disclosure is prepared into an injection type formulation such that a pharmaceutical composition according to the present disclosure may be administered by a method of lightly pricking the injection type formulation into the skin with a 30-gauge thin injection needle or a method of directly applying the injection type formulation to the skin.

A pharmaceutical composition according to the present disclosure may be formulated into a preparation for oral administration or a preparation for non-oral administration along the above-described administration routes.

In case of the preparation for oral administration, the composition according to the present disclosure can be formulated into powder, granule, tablet, pill, sugar-coated table, capsule, liquid, gel, syrup, slurry, suspension, etc. by methods known in the art. For example, the preparation for oral administration may include tablet or sugar-coated tablet which are obtained by mixing an active ingredient with a solid excipient, pulverizing a mixture of the active ingredient and the solid excipient, adding a suitable supplemental agent to a pulverized material, and processing a supplemental agent-added pulverized material into a granule mixture. Examples of a suitable excipient may comprise saccharides including lactose, dextrose, sucrose, sorbitol, mannitol, xylitol, erythritol, maltitol, etc., starches including corn starch, wheat starch, rice starch, potato starch, etc., celluloses including cellulose, methyl cellulose, sodium carboxymethyl cellulose, hydroxypropyl methylcellulose, etc., and fillers including gelatin, polyvinylpyrrolidone, etc. Further, in some cases, crosslinked polyvinylpyrrolidone, agar, alginic acid, sodium alginate, or the like may be added as a disintegrating agent.

The preparation for non-oral administration can be formulated in the form of injection, cream, lotion, ointment for external application, oil, moisturizer, gel, aerosol, and nasal inhaler by methods known in the art. All of these formulations are described in a document, i.e., a prescription generally known in the pharmaceutical field (Remington's Pharmaceutical Science, 15th Edition, 1975, Mack Publishing Company, Easton, Pa. 18042, Chapter 87: Blaug, Seymour).

Total therapeutically effective amount of peptides according to the present disclosure may be administered to patients with single dose or multiple dose of fractionated treatment protocol. An active ingredient included in a pharmaceutical composition according to the present disclosure may vary according to the severity of a disease.

BRIEF DESCRIPTION OF THE DRAWINGS

FIG. 1 is results of preparing random peptide DNA libraries according to an embodiment of the present disclosure.

FIG. 2 is results of checking if specificity for an acetylcholine receptor has been increased in a biopanning step according to an embodiment of the present disclosure.

FIG. 3 illustrates ELISA results for the acetylcholine receptor compared to streptavidin, i.e., a negative control group of a recombinant phage recovered in the biopanning step according to an embodiment of the present disclosure.

FIG. 4 is multiple alignment results of peptides selected by sequencing of a recombinant phage having 1.5 time or more of a signal ratio of the acetylcholine receptor to streptavidin in the ELISA results according to an embodiment of the present disclosure.

FIG. 5 is results of measuring binding ability values of the selected peptides and Synake and Vialox which are a positive control group according to an embodiment of the present disclosure.

FIG. 6 is results of measuring binding ability values of Synake which is a positive control group according to an embodiment of the present disclosure.

FIG. 7 is results of measuring binding ability values of the selected peptides according to an embodiment of the present disclosure.

FIG. 8 is results of comparing binding ability values of deleted peptides for optimization according to an embodiment of the present disclosure.

FIG. 9 is results of measuring binding ability values of the deleted peptides according to an embodiment of the present disclosure.

FIG. 10 is results of measuring affinity values of the deleted peptides according to an embodiment of the present disclosure.

DESCRIPTION OF EXEMPLARY EMBODIMENTS

Hereinafter, the present disclosure will be described in more detail through Examples. It will be obvious to a person having ordinary skill in the art that these examples are illustrative purposes only and are not to be construed to limit the scope of the present disclosure.

Example 1. Preparing Random Peptide Phage Libraries 1-1. Preparing 4 Mer, 5 Mer and 6 Mer Random Peptides and Inserting the Prepared Random Peptides into Vector In order to prepare random peptide libraries (WTWKG (SEQ ID NO:32)(X)$_n$, X=random amino acids, DNA libraries 4mer (TTCTATGCGGCCCAGCTGGCCTGGACATG-GAAGGGANNKNNKNNKNNKGC GGCCGCAGAAACTGTT (SEQ ID NO:34)), 5mer (TTC-TATGCGGCCCAGCTGGCCTGGACATGGAAGG-GANNKNNKNNKNKKNN KGCGGCCGCAGAAACTGTT (SEQ ID NO:35)), and 6mer (TTCTATGCGGCCCAGCTGGCCTGGACATG-GAAGGGANNKNNKNNKNNKNK KNNKGCGGCCGCAGAAACTGTT (SEQ ID NO:36)) were synthesized (Bioneer, Daejeon, Korea).

Double strand insert was amplified by using PCR as two single strand primers (TTCTATGCGGCCCAG(SEQ ID NO:37) and AACAGTTTCTGCGGC(SEQ ID NO:38)). Preparation results of random peptide DNA libraries are illustrated in FIG. 1.

In order to insert the random peptide DNA libraries into a phagemid vector (pIGT), insert DNA amplified using the phagemid vector and PCR was treated with restriction enzymes.

After reacting about 10 μg of the insert DNA with SfiI (New England Biolab (NEB)), Ipswich) and NotI (NEB, Ipswich) for 8 hours, a purified DNA was obtained by using a PCR purification kit. Further, after treating about 10 μg of the phagemid vector with SfiI and NotI for 8 hours and injecting CIAP (Calf Intestinal Alkaline Phosphate) (NEB, Ipswich) into the phagemid vector treated with SfiI and NotI to react CIAP with the phagemid vector treated with SfiI and NotI, a reaction product was purified by using the PCR purification kit. Purification results are illustrated in FIG. 1, and $1.8 \times 10^9$ of 4 mer peptide library DNAs, $3.2 \times 10^8$ of 5 mer peptide library DNAs and $5.9 \times 10^8$ of 6 mer peptide library DNAs were respectively prepared.

After connecting an insert DNA (3 μg) to a phagemid vector (10 μg) at 18° C. for 15 hours by using a T4 DNA ligase (Bioneer, Daejeon, Korea), the DNAs were dissolved in 100 μℓ of a TE buffer by precipitating the phagemid vector connected to the T4 DNA ligase with ethanol.

1.2 Electroporation

After dividing 100 μℓ of a phagemid vector including the respective 4 mer, 5 mer and 6 mer random insert DNAs that had been prepared in the Example 1.1 into 25 phagemid vectors each having 4 μℓ, an electroporation process was performed on the 25 phagemid vectors each having 4 μℓ.

More specifically, after melting a competent cell on ice, mixing 200 μℓ of the competent cell with each of 4 μℓ of phagemid vector solutions including the insert DNAs, and injecting the mixed solutions into a 0.2 cm cuvette that had been cooled and prepared, the resulting materials were put on ice for 1 minute.

After programming an electroporator (BioRAD, Hercules, Calif.) under conditions of 25 μF and 2.5 kV at 25Ω, removing water of the prepared cuvette, and positioning the cuvette in the electric perforator, a pulse was applied to the electroporator (time constant was 4.5 to 5 msec). Then, after immediately inserting the electroporated materials into a LB (Luria Bertani) liquid culture medium including 20 mM of glucose that had been prepared at 37° C. to obtain cells with the total amount of 25 ml, the obtained cells with the total amount of 25 ml were moved to 100 ml test tubes. After culturing the cells while mixing the cells by a speed of 200 rpm at 37° C. for one hour, dividing the cultured cells into 10 μℓ of the cultured cells, and diluting 10 μℓ of the divided cultured cells, 10 μℓ of the diluted cultured cells was spread on an ampicillin agar medium to measure the number of libraries. After injecting cells remained after performing the dividing process along with 20 mM of glucose and 50 μg/ml of ampicillin into 1 L of LB, the cells were cultured at 30° C. for one day. After centrifuging the culture solution to a speed of 4,000 rpm at 4° C. for 20 minutes to remove a supernatant except settled cells from the centrifuged culture solution, re-suspending the supernatant-removed centrifuged culture solution with 40 ml of LB, and injecting glycerol with a final concentration of 20% or more into the re-suspension, the glycerol-injected re-suspension was stored at −80° C.

1.3 Producing Recombinant Phages from Random Peptide Libraries

Recombinant phages were produced from 4 mer, 5 mer and 6 mer random peptide libraries stored at −80° C. in Example 1.2.

After adding 1 ml of the libraries that had been stored at −80° C. to 30 ml of an SB liquid culture medium, a culturing process was performed to obtain culture solutions by mixing the libraries with the SB liquid culture medium to a speed of 200 rpm at 37° C. for 20 minutes. After injecting a helper phage (1010 pfu) and ampicillin (final concentration of 50 μg/ml) into the culture solutions, and a culturing process was performed again under the same conditions for 1 hour. Recombinant phages were produced by moving the culture solutions to 30 ml of an SB liquid culture medium including ampicillin (50 μg/ml) and kanamycin (10 μg/ml) and culturing mixed solutioned of the culture solutions and the SB liquid culture medium under the same conditions for 16 hours or more. After centrifuging the produced recombinant phages to a speed of 5,000 rpm at 4° C. for 10 minutes to obtain supernatants, mixing PEG/NaCl with the supernatants at a volume ratio (v/v) of 5:1, leaving along the mixed solutions on ice for 1 hour, and centrifuging the mixed solutions to a speed of 13,000 rpm at 4° C. for 20 minutes to carefully remove the supernatants, pellets were resuspended in the supernatant-removed centrifuged solutions with 1 ml of PBS (phosphate buffered saline).

Example 2. Method of Screening Peptides to be Linked to an Acetylcholine Receptor 2.1 Biopanning of Acetylcholine Receptor After putting acetylcholine receptor (AchR) alpha 1 (10 µg/ml) into 8 wells of 96 well high binding plates in an amount as much as 50 $\mu\ell$, leaving alone the acetylcholine receptor (AchR) alpha 1 put into the 8 wells at 4° C. overnight, washing the acetylcholine receptor (AchR) alpha 1 put into the 8 wells with 200 $\mu\ell$ of PBS once the next day, putting 200 $\mu\ell$ of 2% BSA (Bovine Serum Albumin) into the acetylcholine receptor (AchR) alpha 1 washed with PBS to obtain a mixture, blocking the mixture at room temperature for 2 hours, and removing all solution from the mixture, a resulting material was washed with 200 $\mu\ell$ of PBS three times.

After mixing the washed resulting material with 400 $\mu\ell$ of a solution including the 4 mer, 5 mer and 6 mer random peptide recombinant phages each prepared in Example 1.3 and 400 $\mu\ell$ of 2% BSA to obtain a mixture, putting the mixture into 8 wells in an amount of 100 $\mu\ell$ per well, the mixture put into the wells was left alone at room temperature for 1 hour, removing all solution from the mixture in the 8 wells, washing the solution-removed mixture with 0.1% PBST (tween-20) three times, putting 0.2 M glycine (pH 2.2) into the washed mixture in an amount of 100 $\mu\ell$ per well to elute the phages for 10 minutes, and collecting the eluted phages in 800 $\mu\ell$ of an E-tube, 200 $\mu\ell$ of 1 M Tris (pH 9.0) was put into the eluted phages collected in the E-tube to obtain a neutralized material.

In order to measure the number of input phages and the number of output phages per each of biopannings, after mixing the neutralized material with E. coli with OD=0.7, the mixture was spread on an agar culture medium including ampicillin. In order to repeatedly perform a panning process, after mixing 500 $\mu\ell$ of the output phages with 5 ml of E. coli to a rotation speed of 200 rpm at 4° C. for 30 minutes, and culturing the output phages mixed with E. coli to obtain a culture medium, a culturing process was performed in the same manner for 30 minutes by adding ampicillin (50 µg/ml) and helper phage ($1 \times 10^{10}$ pfu) to the culture medium. Then, after moving a culture solution to 50 ml of an SB culture medium including ampicillin (50 µg/ml) and kanamycin (10 µg/ml), the culturing process was performed in the same manner for 1 day to obtain a culture solution. After centrifuging the culture solution to a speed of 5,000 rpm at 4° C. for 10 minutes and adding PEG/NaCl [20% PEG(w/v) and 15% NaCl(w/v)] to a supernatant of the centrifuged culture solution at a ratio of 5:1, the mixed solution was settled on ice for 1 hour. After centrifuging the settled solution to a speed of 13,000 rpm at 4° C. for 20 minutes, completely removing a supernatant from the centrifuged solution, and suspending phage pellets with 1 ml of a PBS solution to obtain a suspension, the suspension was used in a second biopanning process. The same method was used in each panning step as described above, the washing processes were performed 3 times, 5 times, 7 times and 10 times respectively, and conditions at which the process of biopanning 6 mer libraries (S6) was performed over 5 times with respect to an acetylcholine receptor protein and results of the input phages and the output phages are shown in the following Table 1.

TABLE 1

| | | S6 Biopanning | | |
|---|---|---|---|---|
| Conditions | Name | Input | Output | Output/Input |
| AchR 10 µg/ml Binding 30° C. Incubation 1 h PBST 0.1% Washing 3 times | $1^{st}$ S6 | $28 * 400 * 10^6 = 1.12 * 10^{10}$ | $21 * 1000 * 10^2 = 2.1 * 10^6$ | $18.75 * 10^{-5}$ |
| AchR 10 µg/ml Binding 30+ C. Incubation 1 h PBST 0.1% Washing 5 times | $2^{nd}$ S6 | $9 * 400 * 10^6 = 3.6 * 10^9$ | $4 * 1000 * 10^2 = 4 * 10^5$ | $11.1 * 10^{-5}$ |
| AchR 10 µg/ml Binding 30° C. Incubation 1 h PBST 0.1% Washing 7 times | $3^{rd}$ S6 | $128 * 400 * 10^6 = 5.12 * 10^{10}$ | $20 * 1000 * 10^2 = 2.0 * 10^6$ | $3.9 * 10^{-5}$ |
| AchR 10 µg/ml Binding 30° C. Incubation 1 h PBST 0.1% Washing 10 times | $4^{th}$ S6 | $79 * 400 * 10^6 = 3.16 * 10^{10}$ | $75 * 1000 * 10^2 = 7.5 * 10^6$ | $23.7 * 10^{-5}$ |
| AchR 10 µg/ml Binding 30° C. Incubation 1 h PBST 0.1% Washing 10 times | $5^{th}$ S6 | $104 * 400 * 10^6 = 4.16 * 10^{10}$ | $82 * 1000 * 10^2 = 8.2 * 10^6$ | $19.7 * 10^{-5}$ |

2.2 ELISA of Input Phages of Acetylcholine Receptor (AchR)

ELISA of respective input phages of the above-mentioned libraries was performed on streptavidin and acetylcholine receptor (AchR).

After putting 10 μg/ml of the acetylcholine receptor into 96 well ELISA plates and putting streptavidins into 10 wells in an amount of 50 μℓ per well, the acetylcholine receptor put into the 96 well ELISA plates and streptavidins put into the 10 wells were left alone at 4° C. for 1 day. Then, after washing all wells with 0.05% PBST three times, blocking the washed wells at room temperature for 2 hours by using 2% BSA diluted by PBS, and removing all of solution from a blocked material, the solution-removed material was washed with 0.05% PBST three times.

After mixing 800 μℓ of third ($3^{rd}$ S6), fourth ($4^{th}$ S6) and fifth ($5^{th}$ S6) input phages, i.e., recombinant phages in Table 1 with 200 μℓ of 10% BSA to obtain mixtures and dividing 3 wells of the mixtures into acetylcholine receptor and streptavidin well in an amount of 100 μℓ, the resulting materials were settled at 30° C. for 1 hour. After washing the settled materials with a 0.05% PBST solution three times and diluting HRP-conjugate anti-M13 antibody (GE Healthcare) to 1:1,000 to obtain a diluted solution, and the washed materials were reacted with the diluted solution at 30° C. for 1 hour. After washing reaction products with 0.05% PBST three times and dividing 100 μℓ of a solution of tetramethylbenzidine (TMB) (BD Science), i.e., a substrate of peroxidase into the washed reaction products to induce a chromogenic reaction, the reaction was stopped by adding 100 μℓ of 1M HCl to the chromogenic reaction-induced materials. Thereafter, absorbance values of the resulting materials were measured at 450 nm. Results of measuring the absorbance values are illustrated in FIG. 2.

2.3 Specific Phage Searching in Acetylcholine Receptor (Colony ELISA)

After inoculating fourth ($4^{th}$ S6) and fifth ($5^{th}$ S6) output phages in Table 1 into *E. coli*, the fourth ($4^{th}$ S6) and fifth ($5^{th}$ S6) output phages inoculated into *E. coli* were spread to obtain about 100 to 200 plaques per plate. After inoculating 50 plaques into 1 ml of an SB-ampicillin (50 μg/ml) culture solution using a sterilized tip, performing a process of shake-culturing the plaque-inoculated culture solutions at 37° C. for 5 hours, and adding 30 μℓ of a helper phage to the shake-cultured solutions, the mixed solutions were cultured to a speed of 200 rpm at 37° C. for 1 day to obtain culture solutions. After centrifuging the culture solutions to a speed of 12,000 rpm for 2 minutes to recover supernatants from the centrifuged culture solutions, and putting 2% BSA into the recovered supernatants, the supernatants having the 2% BSA put thereinto were used for searching the phages.

After putting 5 μg/ml of the acetylcholine receptor into the 96 well ELISA plates and putting streptavidins into 50 wells in an amount of 50 μℓ per well, the acetylcholine receptor put into the 96 well ELISA plates and streptavidins put into the 50 wells were left alone at 4° C. for 1 day. On the next day, after removing proteins of all wells, blocking the removed proteins at room temperature for 2 hours by using 2% BSA, and throwing away solutions from the blocked proteins, resulting materials were washed with 0.05% PBST. After dividing phage solutions amplified per each of clones into all wells in an amount of 100 μℓ, the divided phage solutions were settled at 30° C. for 1 hour. After washing the settled materials with a 0.05% PBST solution three times, diluting HRP-conjugate anti-M13 antibody (GE Healthcare) to 1:2,000 to obtain a diluted solution, and dividing the washed materials into the diluted solution in an amount of 100 μℓ, the washed materials were reacted with the diluted solution at 30° C. for 1 hour. After washing reaction products with 0.05% PBST three times and dividing 100 μℓ of the TMB solution into the washed reaction products to induce a chromogenic reaction, the reaction was stopped by adding 100 μℓ of 1M $H_2SO_4$ to the chromogenic reaction-induced materials. Thereafter, results are illustrated in FIG. 3.

Referring to FIG. 3, sequencing was requested by purifying plasmids of phages having 1.5 time or more of an acetylcholine receptor signal compared to streptavidin (Bioneer, Deajon, Korea). GATTACGCCAAGCTTTGGAGC (SEQ ID NO:39) was used as a sequencing primer.

Peptide sequences having specific binding abilities in the acetylcholine receptor through sequencing are shown FIG. 4 and the following Table 2.

TABLE 2

| | Peptide sequences | |
|---|---|---|
| Name | Sequences | Duplication number |
| S6_1 | WTWKGKGTLNR | 6/16 |
| S6_2 | WTWKGRKSLLR | 1/16 |
| S6_3 | WTWKGEDKGKN | 1/16 |
| S6_4 | WTWKGRDKLQM | 1/16 |
| S6_5 | WTWKGQLGQLS | 1/16 |
| S6_6 | WTWKGGRLSAS | 1/16 |
| S6_7 | WTWKGRQLNNQ | 1/16 |
| S6_8 | WTWKGDNLQNN | 1/16 |
| S6_9 | WTWKGLYQRLG | 1/16 |
| S6_10 | WTWKGNKQVKF | 1/16 |
| S6_11 | WTWKGETYDSK | 1/16 |

Example 3. Experiment of Comparing Acetylcholine Binding Forces of Discovered Peptides S6_1 (SEQ ID NO:23, WTWKGKGTLNR), S6_2 (SEQ ID NO: 2 4, WTWKGRKSLLR), S6_3 (SEQ ID NO: 25, WTWKGEDKGKN), S6_4 (SEQ ID NO: 26, WTWKGRDKLQM) showing sequence similarities through multiple alignments among the peptides in Table 2 were synthesized.

A surface plasmon resonance (SPR) experiment was progressed using a biosensor chip to compare binding forces for the acetylcholine receptors thereof (Biacore 3000, Biacore AB, Uppsala, Sweden). After fixing selected acetylcholine receptor proteins to a CMS chip (Biacore) using EDC/NHS, association and dissociation were observed for up to 500 seconds. A binding force comparing experiment was carried out under observation conditions of a running buffer of 20 mM Tris (pH 7.4), a speed of 30 μℓ/min, and a peptide concentration of 10 μM (S6_1, S6_2, S6_3, S6_4). Results of the binding force comparing experiment are shown in FIG. 5.

Example 4. Experiment of Comparing Binding Forces of Discovered Peptides S6_1 and a Positive Control Group A surface plasmon resonance (SPR) experiment was progressed using a biosensor chip to compare binding forces for acetylcholine receptors of S6_1 (SEQ ID NO: 23, WTWKGKGTLNR), i.e., discovered peptides and S6_1_C6 (SEQ ID NO: 31, KGTLNR), i.e., a deleted form, and Synake and Vialox, i.e., a positive control group (Biacore 3000, Biacore AB, Uppsala, Sweden).

After fixing selected acetylcholine receptor proteins to a CMS chip (Biacore) using EDC/NHS, association and dissociation were observed for up to 500 seconds. A binding force comparing experiment was carried out under observation conditions of a running buffer of 20 mM Tris (pH 7.4), a speed of 30 µℓ/min, and a peptide concentration of 10 µM (Synake, Vialox, S6_1, S6_1_C6). Results of the binding force comparing experiment are shown in FIG. 6.

Example 5. Measuring Affinity Values of S6_1 Peptides and Synake Peptides

A surface plasmon resonance (SPR) experiment was progressed using a biosensor chip to check affinity values for acetylcholine receptors of S6_1 (SEQ ID NO: 23, WTWKGKGTLNR), i.e., discovered peptides and Synake, i.e., a positive control group (Biacore 3000, Biacore AB, Uppsala, Sweden). After fixing the acetylcholine receptors to a CMS chip (Biacore) using EDC/NHS, association and dissociation were observed for up to 500 seconds. A binding ability comparing experiment was carried out under observation conditions of a running buffer of 20 mM Tris (pH 7.4), a speed of 30 µℓ/min, a concentration of 10 to 50 µM (Synake), and a concentration of 0.1 to 10 µM (peptides S6_1). Respective results of the binding ability comparing experiment are shown in FIG. 7 (Synake) and FIG. 8 (peptides S6_1).

Example 6. Experiment of Comparing Optimizations and Binding Forces of Peptides of S6_1

S6_1_C10 (SEQ ID NO: 27, TWKGKGTLNR), S6_1_C9 (SEQ ID NO: 28, WKGKGTLNR), S6_1_C10 end (SEQ ID NO: 29, WTWKGKGTLN), and S6_1_C9 end (SEQ ID NO: 30, WTWKGKGTL), i.e., peptides which each have one amino acid and two amino acids respectively removed from N-terminal and C-terminal thereof were synthesized to optimize S6_1.

A surface plasmon resonance (SPR) experiment was progressed using a biosensor chip to compare binding forces for acetylcholine receptors of these peptides (Biacore 3000, Biacore AB, Uppsala, Sweden).

After fixing selected acetylcholine receptor proteins to a CMS chip (Biacore) using EDC/NHS, association and dissociation were observed for up to 500 seconds. An experiment of comparing optimizations and binding forces of the peptides was carried out under observation conditions of a running buffer of 20 mM Tris (pH 7.4), a speed of 30 µℓ/min, and a peptide concentration of 10 µM (Synake, Vialox, S6_1, S6_1_C10, S6_1_C9, S6_1_C10 end, S6_1_C9 end, and S6_1_C6). Experiment results of comparing the optimizations and binding forces of the peptides are shown in FIG. 9.

Example 7. Measuring Affinity Values of S6_1_C9 Peptides

A surface plasmon resonance (SPR) experiment was progressed using a biosensor chip to check affinity values for acetylcholine receptors of optimized S6_1_C9 peptides (SEQ ID NO: 28, WKGKGTLNR) prepared in Example 6 (Biacore 3000, Biacore AB, Uppsala, Sweden).

After fixing selected acetylcholine receptor proteins to a CMS chip (Biacore) using EDC/NHS, association and dissociation were observed for up to 500 seconds. An experiment of measuring affinity values of the peptides was carried out under observation conditions of a running buffer of 20 mM Tris (pH 7.4), a speed of 30 µℓ/min, and a concentration of 0.1 to 0.5 µM (peptides S6_1_C9).

Experiment results of measuring the affinity values of the peptides are shown in FIG. 10. Referring to FIG. 10, it can be confirmed that the S6_1_C9 peptides (SEQ ID NO: 28, WKGKGTLNR) exhibit about 100 times higher binding abilities than Synake for acetylcholine.

Peptides according to the present disclosure suppress secretion of acetylcholine by having a high binding strength with an acetylcholine receptor, thereby strongly binding the peptides to acetylcholine. Therefore, a cosmetic composition and a pharmaceutical composition comprising peptides according to the present disclosure as an active ingredient exhibit an excellent wrinkle ameliorating effect.

Although the present disclosure has been described along with the accompanying drawings, this is only one of various examples including the gist of the present disclosure and has an object of enabling a person having ordinary skill in the art to easily practice the invention. Accordingly, it is evident that the present disclosure is not limited to the aforementioned examples. Accordingly, the range of protection of the present disclosure should be interpreted based on the following claims, and all of technological spirits within the equivalents of the present disclosure may fall within the range of right of the present disclosure by changes, substitutions and replacements without departing from the gist of the present disclosure. Furthermore, it is evident that the configurations of some drawings have been provided to more clearly describe configurations and have been more exaggerated or reduced than actual configurations.

What is claimed is:

1. An acetylcholine receptor-binding peptide consisting of an amino acid sequence represented by one selected from the group consisting of SEQ ID NO: 12 to SEQ ID NO: 22.

2. A cosmetic composition for wrinkle amelioration comprising the peptide of claim 1 as an active ingredient.

3. A pharmaceutical composition for wrinkle amelioration comprising the peptide of claim 1 as an active ingredient.

* * * * *

SEQUENCE LISTING

```
<160> NUMBER OF SEQ ID NOS: 39

<210> SEQ ID NO 1
<211> LENGTH: 6
<212> TYPE: PRT
<213> ORGANISM: Artificial Sequence
<220> FEATURE:
<223> OTHER INFORMATION: Ach-R

<400> SEQUENCE: 1

Lys Gly Thr Leu Asn Arg
```

```
<210> SEQ ID NO 2
<211> LENGTH: 6
<212> TYPE: PRT
<213> ORGANISM: Artificial Sequence
<220> FEATURE:
<223> OTHER INFORMATION: Ach-R

<400> SEQUENCE: 2

Arg Lys Ser Leu Leu Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Ach-R

<400> SEQUENCE: 3

Glu Asp Lys Gly Lys Asn
1               5

<210> SEQ ID NO 4
<211> LENGTH: 6
<212> TYPE: PRT
<213> ORGANISM: Artificial Sequence
<220> FEATURE:
<223> OTHER INFORMATION: Ach-R

<400> SEQUENCE: 4

Arg Asp Lys Leu Gln Met
1               5

<210> SEQ ID NO 5
<211> LENGTH: 6
<212> TYPE: PRT
<213> ORGANISM: Artificial Sequence
<220> FEATURE:
<223> OTHER INFORMATION: Ach-R

<400> SEQUENCE: 5

Gln Leu Gly Gln Leu Ser
1               5

<210> SEQ ID NO 6
<211> LENGTH: 6
<212> TYPE: PRT
<213> ORGANISM: Artificial Sequence
<220> FEATURE:
<223> OTHER INFORMATION: Ach-R

<400> SEQUENCE: 6

Gly Arg Leu Ser Ala Ser
1               5

<210> SEQ ID NO 7
<211> LENGTH: 6
<212> TYPE: PRT
<213> ORGANISM: Artificial Sequence
<220> FEATURE:
<223> OTHER INFORMATION: Ach-R

<400> SEQUENCE: 7

Arg Gln Leu Asn Asn Gln
1               5
```

```
<210> SEQ ID NO 8
<211> LENGTH: 6
<212> TYPE: PRT
<213> ORGANISM: Artificial Sequence
<220> FEATURE:
<223> OTHER INFORMATION: Ach-R

<400> SEQUENCE: 8

Asp Asn Leu Gln Asn Asn
1               5

<210> SEQ ID NO 9
<211> LENGTH: 6
<212> TYPE: PRT
<213> ORGANISM: Artificial Sequence
<220> FEATURE:
<223> OTHER INFORMATION: Ach-R

<400> SEQUENCE: 9

Leu Tyr Gln Arg Leu Gly
1               5

<210> SEQ ID NO 10
<211> LENGTH: 6
<212> TYPE: PRT
<213> ORGANISM: Artificial Sequence
<220> FEATURE:
<223> OTHER INFORMATION: Ach-R

<400> SEQUENCE: 10

Asn Lys Gln Val Lys Phe
1               5

<210> SEQ ID NO 11
<211> LENGTH: 6
<212> TYPE: PRT
<213> ORGANISM: Artificial Sequence
<220> FEATURE:
<223> OTHER INFORMATION: Ach-R

<400> SEQUENCE: 11

Glu Thr Tyr Asp Ser Lys
1               5

<210> SEQ ID NO 12
<211> LENGTH: 11
<212> TYPE: PRT
<213> ORGANISM: Artificial Sequence
<220> FEATURE:
<223> OTHER INFORMATION: Ach-R

<400> SEQUENCE: 12

Trp Thr Trp Lys Gly Lys Gly Thr Leu Asn Arg
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Ach-R

<400> SEQUENCE: 13

Trp Thr Trp Lys Gly Arg Lys Ser Leu Leu Arg
1               5                   10
```

```
<210> SEQ ID NO 14
<211> LENGTH: 11
<212> TYPE: PRT
<213> ORGANISM: Artificial Sequence
<220> FEATURE:
<223> OTHER INFORMATION: Ach-R

<400> SEQUENCE: 14

Trp Thr Trp Lys Gly Glu Asp Lys Gly Lys Asn
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Ach-R

<400> SEQUENCE: 15

Trp Thr Trp Lys Gly Arg Asp Lys Leu Gln Met
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Ach-R

<400> SEQUENCE: 16

Trp Thr Trp Lys Gly Gln Leu Gly Gln Leu Ser
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Ach-R

<400> SEQUENCE: 17

Trp Thr Trp Lys Gly Gly Arg Leu Ser Ala Ser
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Ach-R

<400> SEQUENCE: 18

Trp Thr Trp Lys Gly Arg Gln Leu Asn Asn Gln
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Ach-R

<400> SEQUENCE: 19

Trp Thr Trp Lys Gly Asp Asn Leu Gln Asn Asn
1               5                   10
```

```
<210> SEQ ID NO 20
<211> LENGTH: 11
<212> TYPE: PRT
<213> ORGANISM: Artificial Sequence
<220> FEATURE:
<223> OTHER INFORMATION: Ach-R

<400> SEQUENCE: 20

Trp Thr Trp Lys Gly Leu Tyr Gln Arg Leu Gly
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Ach-R

<400> SEQUENCE: 21

Trp Thr Trp Lys Gly Asn Lys Gln Val Lys Phe
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Ach-R

<400> SEQUENCE: 22

Trp Thr Trp Lys Gly Glu Thr Tyr Asp Ser Lys
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Ach-R

<400> SEQUENCE: 23

Trp Thr Trp Lys Gly Lys Gly Thr Leu Asn Arg
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Ach-R

<400> SEQUENCE: 24

Trp Thr Trp Lys Gly Arg Lys Ser Leu Leu Arg
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Ach-R

<400> SEQUENCE: 25

Trp Thr Trp Lys Gly Glu Asp Lys Gly Lys Asn
1               5                   10

<210> SEQ ID NO 26
```

```
<211> LENGTH: 11
<212> TYPE: PRT
<213> ORGANISM: Artificial Sequence
<220> FEATURE:
<223> OTHER INFORMATION: Ach-R

<400> SEQUENCE: 26

Trp Thr Trp Lys Gly Arg Asp Lys Leu Gln Met
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Ach-R

<400> SEQUENCE: 27

Thr Trp Lys Gly Lys Gly Thr Leu Asn Arg
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Ach-R

<400> SEQUENCE: 28

Trp Lys Gly Lys Gly Thr Leu Asn Arg
1               5

<210> SEQ ID NO 29
<211> LENGTH: 10
<212> TYPE: PRT
<213> ORGANISM: Artificial Sequence
<220> FEATURE:
<223> OTHER INFORMATION: Ach-R

<400> SEQUENCE: 29

Trp Thr Trp Lys Gly Lys Gly Thr Leu Asn
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Ach-R

<400> SEQUENCE: 30

Trp Thr Trp Lys Gly Lys Gly Thr Leu
1               5

<210> SEQ ID NO 31
<211> LENGTH: 6
<212> TYPE: PRT
<213> ORGANISM: Artificial Sequence
<220> FEATURE:
<223> OTHER INFORMATION: Ach-R

<400> SEQUENCE: 31

Lys Gly Thr Leu Asn Arg
1               5

<210> SEQ ID NO 32
<211> LENGTH: 5
```

```
<212> TYPE: PRT
<213> ORGANISM: Artificial Sequence
<220> FEATURE:
<223> OTHER INFORMATION: Ach-R

<400> SEQUENCE: 32

Trp Thr Trp Lys Gly
1               5

<210> SEQ ID NO 33
<211> LENGTH: 4
<212> TYPE: PRT
<213> ORGANISM: Artificial Sequence
<220> FEATURE:
<223> OTHER INFORMATION: Ach-R

<400> SEQUENCE: 33

Thr Trp Lys Gly
1

<210> SEQ ID NO 34
<211> LENGTH: 66
<212> TYPE: DNA
<213> ORGANISM: Artificial Sequence
<220> FEATURE:
<223> OTHER INFORMATION: DNA libraries 4mer
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t

<400> SEQUENCE: 34
ttctatgcgg cccagctggc ctggacatgg aagggannkn nknnknnkgc ggccgcagaa    60
actgtt                                                              66

<210> SEQ ID NO 35
<211> LENGTH: 69
<212> TYPE: DNA
<213> ORGANISM: Artificial Sequence
<220> FEATURE:
<223> OTHER INFORMATION: DNA libraries 5mer
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)
<223> OTHER INFORMATION: n is a, c, g, or t
<220> FEATURE:
<221> NAME/KEY: misc_feature
<222> LOCATION: (49)..(50)
```

<223> OTHER INFORMATION: n is a, c, g, or t

<400> SEQUENCE: 35
ttctatgcgg cccagctggc ctggacatgg aagggannkn nknnknkknn kgcggccgca    60
gaaactgtt                                                           69

<210> SEQ ID NO 36
<211> LENGTH: 72
<212> TYPE: DNA
<213> ORGANISM: Artificial Sequence
<220> FEATURE:
<223> OTHER INFORMATION: DNA libraries 6mer
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 36
ttctatgcgg cccagctggc ctggacatgg aagggannkn nknnknnknk knnkgcggcc    60
gcagaaactg tt                                                       72

<210> SEQ ID NO 37
<211> LENGTH: 15
<212> TYPE: DNA
<213> ORGANISM: Artificial Sequence
<220> FEATURE:
<223> OTHER INFORMATION: PCR primer

<400> SEQUENCE: 37
ttctatgcgg cccag                                                    15

<210> SEQ ID NO 38
<211> LENGTH: 15
<212> TYPE: DNA
<213> ORGANISM: Artificial Sequence
<220> FEATURE:
<223> OTHER INFORMATION: PCR primer

```
<400> SEQUENCE: 38
aacagtttct gcggc                                                  15

<210> SEQ ID NO 39
<211> LENGTH: 21
<212> TYPE: DNA
<213> ORGANISM: Artificial Sequence
<220> FEATURE:
<223> OTHER INFORMATION: sequencing primer

<400> SEQUENCE: 39
gattacgcca agctttggag c                                           21
```